(12) United States Patent
Huang et al.

(10) Patent No.: US 12,033,365 B2
(45) Date of Patent: Jul. 9, 2024

(54) IMAGE PROCESSING METHOD AND APPARATUS AND STORAGE MEDIUM

(71) Applicant: Tsinghua University, Beijing (CN)

(72) Inventors: Gao Huang, Beijing (CN); Shiji Song, Beijing (CN); Chaoqun Du, Beijing (CN)

(73) Assignee: Tsinghua University, Beijing (CN)

( * ) Notice: Subject to any disclaimer, the term of this patent is extended or adjusted under 35 U.S.C. 154(b) by 394 days.

(21) Appl. No.: 17/562,945

(22) Filed: Dec. 27, 2021

(65) Prior Publication Data

US 2022/0237883 A1    Jul. 28, 2022

(30) Foreign Application Priority Data

Jan. 25, 2021   (CN) .......................... 202110095599.1

(51) Int. Cl.
| | |
|---|---|
| G06V 10/26 | (2022.01) |
| G06T 7/11 | (2017.01) |
| G06V 10/77 | (2022.01) |
| G06V 10/774 | (2022.01) |
| G06V 10/776 | (2022.01) |
| G16H 30/40 | (2018.01) |

(Continued)

(52) U.S. Cl.
CPC ............... *G06V 10/26* (2022.01); *G06T 7/11* (2017.01); *G06V 10/7715* (2022.01); *G06V 10/7747* (2022.01); *G06V 10/776* (2022.01); *G16H 30/40* (2018.01); *G16H 50/20* (2018.01); *G06T 2207/10081* (2013.01); *G06V 10/82* (2022.01); *G06V 2201/031* (2022.01)

(58) Field of Classification Search
CPC ............... G06V 10/26; G06V 10/7747; G06V 10/7715; G06V 10/776; G06T 7/11; G06H 50/20; G06H 30/40
USPC ........................................................ 382/128
See application file for complete search history.

(56) References Cited

U.S. PATENT DOCUMENTS

| | | | |
|---|---|---|---|
| 10,922,816 B2 * | 2/2021 | Huang | G16H 30/40 |
| 11,580,400 B1 * | 2/2023 | Yan | G06N 3/04 |

(Continued)

FOREIGN PATENT DOCUMENTS

CN    111429464 A    7/2020

*Primary Examiner* — William D Titcomb
(74) *Attorney, Agent, or Firm* — Bayramoglu Law Offices LLC

(57) ABSTRACT

An image processing method and apparatus and a storage medium, wherein the method particularly includes firstly acquiring an image-to-be-trained sample and a label segmentation image corresponding to the image-to-be-trained sample; inputting the image-to-be-trained sample into an image segmentation model to be trained, obtaining a first image feature of a last one output layer in the image segmentation model and a second image feature of a second last output layer when the image-to-be-trained sample is being extracted by using the image segmentation model, outputting the corresponding segmented-image samples; based on the label segmentation image and the segmented-image samples, calculating the model loss function, optimizing the model parameter, and generating the image segmentation model that has been optimized; and inputting an acquired image to be processed into the image segmentation model that has been optimized, and generating segmented images corresponding to the image to be processed.

18 Claims, 3 Drawing Sheets

(51) Int. Cl.
*G16H 50/20* (2018.01)
*G06V 10/82* (2022.01)

(56) References Cited

U.S. PATENT DOCUMENTS

| | | | |
|---|---|---|---|
| 2014/0118494 A1* | 5/2014 | Wu | G06T 7/20 |
| | | | 348/E13.02 |
| 2020/0065969 A1* | 2/2020 | Huang | G06V 10/82 |
| 2020/0320726 A1* | 10/2020 | An | G06T 7/55 |
| 2021/0358127 A1* | 11/2021 | Jagadeesh | G06F 17/18 |
| 2021/0374478 A1* | 12/2021 | Lin | G06F 18/214 |
| 2022/0138931 A1* | 5/2022 | Palma | G06T 7/0012 |
| | | | 382/128 |
| 2022/0277434 A1* | 9/2022 | Yumiba | G01B 15/00 |
| 2022/0398783 A1* | 12/2022 | Hu | G06T 3/4046 |
| 2023/0274418 A1* | 8/2023 | Arberet | G16H 30/40 |
| | | | 382/128 |

* cited by examiner

IMAGE PROCESSING METHOD AND APPARATUS AND STORAGE MEDIUM

CROSS REFERENCE OF RELATED APPLICATIONS

This application is based upon and claims priority to Chinese Patent Application No. 202110095599.1, filed on Jan. 25, 2021, the entire contents of which are incorporated herein by reference.

TECHNICAL FIELD

The present application relates to the technical field of computers, and particularly relates to an image processing method and apparatus and a storage medium.

BACKGROUND

Medical image diagnosis refers to, by using the non-intrusive action of a certain physical medium, such as electromagnetic wave and ultrasonic wave, acquiring the internal image data of human body, for example acquiring the internal density data of human body by using a CT method, thereby evaluating the health status of the human body. Doctors generally make the final medical diagnosis by combining the medical images and the routine disease checking methods in the clinical practice. For modern medicine, the medical image diagnosis means has become an indispensable step in clinical diagnosis, and therefore the interpretation of the medical-image data has become an important and critical work of doctors.

However, medical image diagnosis has high requirements on the segmentation precision and the stability. Therefore, currently the interpretation of medical-image data still relies on the interpretation by experienced image doctors. The diagnostic results of such a diagnostic mode are susceptible to the limitation by the personal experience and capacity of the doctors, and the accuracy rate is difficult to be ensured in the processing of data of a large scale due to fatigue. Furthermore, medical-image data have a complicated structure, which results in a very high misdiagnosis rate of the artificial diagnosis.

SUMMARY

The embodiments of the present application provide an image processing method, which overcomes the problem of a low precision of image segmentation.

the method comprises:
  acquiring at least one image-to-be-trained sample and a label segmentation image corresponding to the image-to-be-trained sample;
  inputting the image-to-be-trained sample into an image segmentation model to be trained, obtaining a first image feature of a last one output layer in the image segmentation model and a second image feature of a second last output layer when the image-to-be-trained sample is being extracted by using the image segmentation model, and based on the first image feature and the second image feature, outputting corresponding segmented-image samples respectively;
  based on the label segmentation image and the segmented-image samples, calculating a model loss function of the image segmentation model, optimizing a model parameter of the image segmentation model by using the model loss function, and generating the image segmentation model that has been optimized; and
  inputting an acquired image to be processed into the image segmentation model that has been optimized, and generating segmented images corresponding to the image to be processed.

Optionally, the step of obtaining the first image feature of the last one output layer in the image segmentation model and the second image feature of the second last output layer when the image-to-be-trained sample is being extracted by using the image segmentation model comprises:
  by using a convolution operation in which a convolution kernel is a first numerical value, adjusting individually a channel dimension of the first image feature and a channel dimension of the second image feature to a preset channel-dimension numerical value.

Optionally, between the step of, based on the first image feature and the second image feature, outputting the corresponding segmented-image samples respectively and the step of calculating the model loss function of the image segmentation model, the method further comprises:
  performing a max-pooling operation to the label segmentation image, and adjusting an image scale comprising the channel dimension of the label segmentation image to a preset image scale comprising the preset channel-dimension numerical value.

Optionally, the step of calculating the model loss function of the image segmentation model comprises:
  calculating a cross-entropy loss between at least one of the label segmentation images obtained after the max-pooling operation and the corresponding segmented-image samples, and using an average value of a sum of a predetermined quantity of the acquired cross-entropy losses as the model loss function of the image segmentation model.

Optionally, the step of optimizing the model parameter of the image segmentation model by using the model loss function comprises:
  initializing the model parameter and a training iteration number of the image segmentation model;
  performing reverse derivation to the model loss function, updating the model parameter based on a gradient corresponding to the model loss function after the reverse derivation, and accumulating a time quantity of the updating till the training iteration number; and
  executing repeatedly the step of acquiring the at least one image-to-be-trained sample and the label segmentation image corresponding to the image-to-be-trained sample to the step of updating the model parameter based on the gradient corresponding to the model loss function after the reverse derivation, till the current training iteration number is greater than the total training iteration number, stopping the optimization, and saving the current image segmentation model that has been optimized.

In another embodiment of the present disclosure, there is provided an image processing apparatus, wherein the apparatus comprises:
  an acquiring module configured for acquiring at least one image-to-be-trained sample and a label segmentation image corresponding to the image-to-be-trained sample;
  an extracting module configured for inputting the image-to-be-trained sample into an image segmentation model to be trained, obtaining a first image feature of a last one output layer in the image segmentation model and a second image feature of a second last output layer when the image-to-be-trained sample is being extracted by using the image segmentation model, and based on the first image feature and the second image feature, outputting corresponding segmented-image samples respectively;

a training module configured for, based on the label segmentation image and the segmented-image samples, calculating a model loss function of the image segmentation model, optimizing a model parameter of the image segmentation model by using the model loss function, and generating the image segmentation model that has been optimized; and a generating module configured for inputting an acquired image to be processed into the image segmentation model that has been optimized, and generating segmented images corresponding to the image to be processed.

Optionally, the extracting module is further configured for:

by using a convolution operation in which a convolution kernel is a first numerical value, adjusting individually a channel dimension of the first image feature and a channel dimension of the second image feature to a preset channel-dimension numerical value.

Optionally, the apparatus further comprises:

a pooling module configured for performing a max-pooling operation to the label segmentation image, and adjusting an image scale comprising the channel dimension of the label segmentation image to a preset image scale comprising the preset channel-dimension numerical value.

In another embodiment of the present disclosure, there is provided a non-transient computer-readable storage medium, wherein the non-transient computer-readable storage medium stores an instruction, and the instruction, when executed by a processor, enables the processor to implement the steps of the image processing method stated above.

In another embodiment of the present disclosure, there is provided a terminal device, wherein the terminal device comprises a processor, and the processor is configured for implementing the steps of the image processing method stated above.

Based on the above embodiments, the present disclosure comprises firstly acquiring at least one image-to-be-trained sample and a label segmentation image corresponding to the image-to-be-trained sample; secondly, inputting the image-to-be-trained sample into an image segmentation model to be trained, obtaining a first image feature of a last one output layer in the image segmentation model and a second image feature of a second last output layer when the image-to-be-trained sample is being extracted by using the image segmentation model, and based on the first image feature and the second image feature, outputting corresponding segmented-image samples respectively; further, based on the label segmentation image and the segmented-image samples, calculating a model loss function of the image segmentation model, optimizing a model parameter of the image segmentation model by using the model loss function, and generating the image segmentation model that has been optimized; and finally, inputting an acquired image to be processed into the image segmentation model that has been optimized, and generating segmented images corresponding to the image to be processed. The embodiments of the present application, by introducing the multilayer decoded and outputted features, further improve the quality of the hidden-layer features, increase the segmentation precision, effectively reduce the segmentation errors without increasing the inference time and the computational complexity, and improve the recognition efficiency and accuracy of the model.

BRIEF DESCRIPTION OF THE DRAWINGS

In order to more clearly illustrate the technical solutions of the embodiments of the present application, the figures that are required to describe the embodiments will be briefly introduced below. It should be understood that the following figures merely show certain embodiments of the present application, and thus should not be considered as a limitation on the scope, and a person skilled in the art can obtain other relevant figures according to these figures without paying creative work.

DETAILED DESCRIPTION OF THE EMBODIMENTS

The technical solutions of the embodiments of the present application will be clearly and completely described below with reference to the drawings of the embodiments of the present application. Apparently, the described embodiments are merely certain embodiments of the present application, rather than all of the embodiments. All of the other embodiments that a person skilled in the art obtains on the basis of the embodiments of the present application without paying creative work fall within the protection scope of the present application.

The terms "first", "second", "third", "fourth" and so on (if necessary) in the description, the claims and the drawings of the present disclosure are intended to distinguish similar objects, and are not necessarily used to describe a particular order or sequence. It should be understood that the data so used may be interchanged in suitable cases, whereby the embodiments of the present disclosure described herein can be implemented in other sequences than those illustrated or described herein. Moreover, the terms "comprise" and "have" and any variation thereof are intended to cover non-exclusive inclusions. For example, a process, method, system, product or device that comprises a series of steps or units is not necessarily limited to those steps or units clearly listed, but may comprise other steps or units that are not clearly listed or that are inherent to the process, method, product or device.

Figure 1:
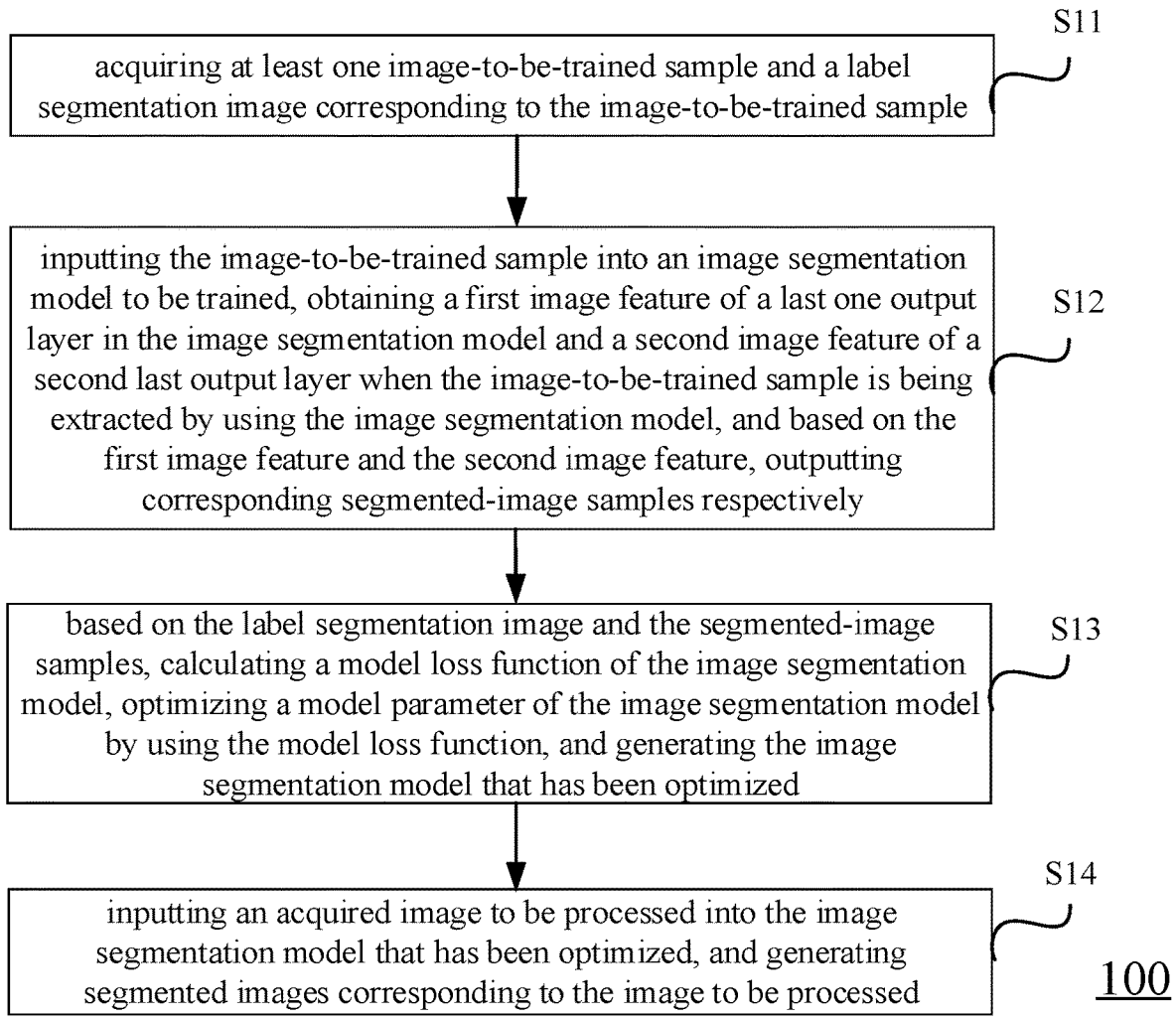
FIG. 1 shows a schematic flow chart of the image processing method according to an embodiment 100 of the present application.

In view of the problems in the prior art, the embodiments of the present application provide an image processing method, which is mainly suitable for the technical field of computers, and is especially suitable for the technical field of medical image analysis methods. Based on the deep-learning algorithm and by using the deep-supervision method, image segmentation is performed to the image to be trained, for example lesion segmentation by using electronic-computer tomography, and a suitable hidden-layer-assisted loss function is introduced into the image segmentation model to be trained. It, by suitably using an assisting classifier as the feedback of the feature quality at the hidden layer, directly influences the updating of the weight of the hidden layer, improves the quality of the hidden-layer features, significantly reduces the test error, and obtains results of a higher segmentation precision, to realize an image processing method. The following particular embodiments may be combined with each other, and the same or similar concepts or processes may not be discussed repeatedly in some of the embodiments. As shown in FIG. 1, FIG. 1 is a schematic flow chart of the image processing method according to an embodiment 100 of the present application. The detailed steps are as follows:

Step S11: acquiring at least one image-to-be-trained sample and a label segmentation image corresponding to the image-to-be-trained sample.

In this step, the label segmentation image acquired in the embodiment of the present application is the real value corresponding to the image-to-be-trained sample, and the label segmentation image participates in the training of the image segmentation model as the training label of the image-to-be-trained sample.

Step S12: inputting the image-to-be-trained sample into an image segmentation model to be trained, obtaining a first image feature of a last one output layer in the image segmentation model and a second image feature of a second last output layer when the image-to-be-trained sample is being extracted by using the image segmentation model, and based on the first image feature and the second image feature, outputting corresponding segmented-image samples respectively.

In this step, the image segmentation model according to the embodiments of the present application uses a Unet model as the basic architecture, wherein the model parameter of the image segmentation model is Θ, and at least one acquired image-to-be-trained sample $x_i$ is used as the input of the image segmentation model, and sequentially passes through an encoder and a decoder in the image segmentation model. A first image feature of the last one output layer in the image segmentation model and a second image feature of the second last output layer when the image-to-be-trained sample is being extracted by using the image segmentation model are obtained. Further, processes such as normalization, activation of the maximum value and inhibition of the other small values are performed by using a soft-max activation function along the channel dimension pixel by pixel, to individually generate the segmented-image samples corresponding to the first image feature and the second image feature. The segmented-image sample refers to a segmentation probability graph that is predicted based on the image features.

Step S13: based on the label segmentation image and the segmented-image samples, calculating a model loss function of the image segmentation model, optimizing a model parameter of the image segmentation model by using the model loss function, and generating the image segmentation model that has been optimized.

In this step, the model loss function of the image segmentation model is calculated by using the label segmentation image as the real value and the predicted segmented-image samples. Further, this step comprises performing reverse derivation to the model loss function, optimizing the model parameter by using the parameter gradient obtained after the reverse derivation, and, based on the model parameter that has been optimized, generating the image segmentation model that has been optimized.

Step S14: inputting an acquired image to be processed into the image segmentation model that has been optimized, and generating segmented images corresponding to the image to be processed.

In this step, based on the image segmentation model that has been completely trained, the image to be processed that is required to be predicted is processed, to generate the segmented images corresponding to the image to be processed.

As stated above, based on the above embodiments, the method comprises firstly acquiring at least one image-to-be-trained sample and a label segmentation image corresponding to the image-to-be-trained sample; secondly, inputting the image-to-be-trained sample into an image segmentation model to be trained, obtaining a first image feature of a last one output layer in the image segmentation model and a second image feature of a second last output layer when the image-to-be-trained sample is being extracted by using the image segmentation model, and based on the first image feature and the second image feature, outputting corresponding segmented-image samples respectively; further, based on the label segmentation image and the segmented-image samples, calculating a model loss function of the image segmentation model, optimizing a model parameter of the image segmentation model by using the model loss function, and generating the image segmentation model that has been optimized; and finally, inputting an acquired image to be processed into the image segmentation model that has been optimized, and generating segmented images corresponding to the image to be processed. The embodiments of the present application, by introducing the multilayer decoded and outputted features, further improve the quality of the hidden-layer features, increase the segmentation precision, effectively reduce the segmentation errors without increasing the inference time and the computational complexity, and improve the recognition efficiency and accuracy of the model.

Figure 2:
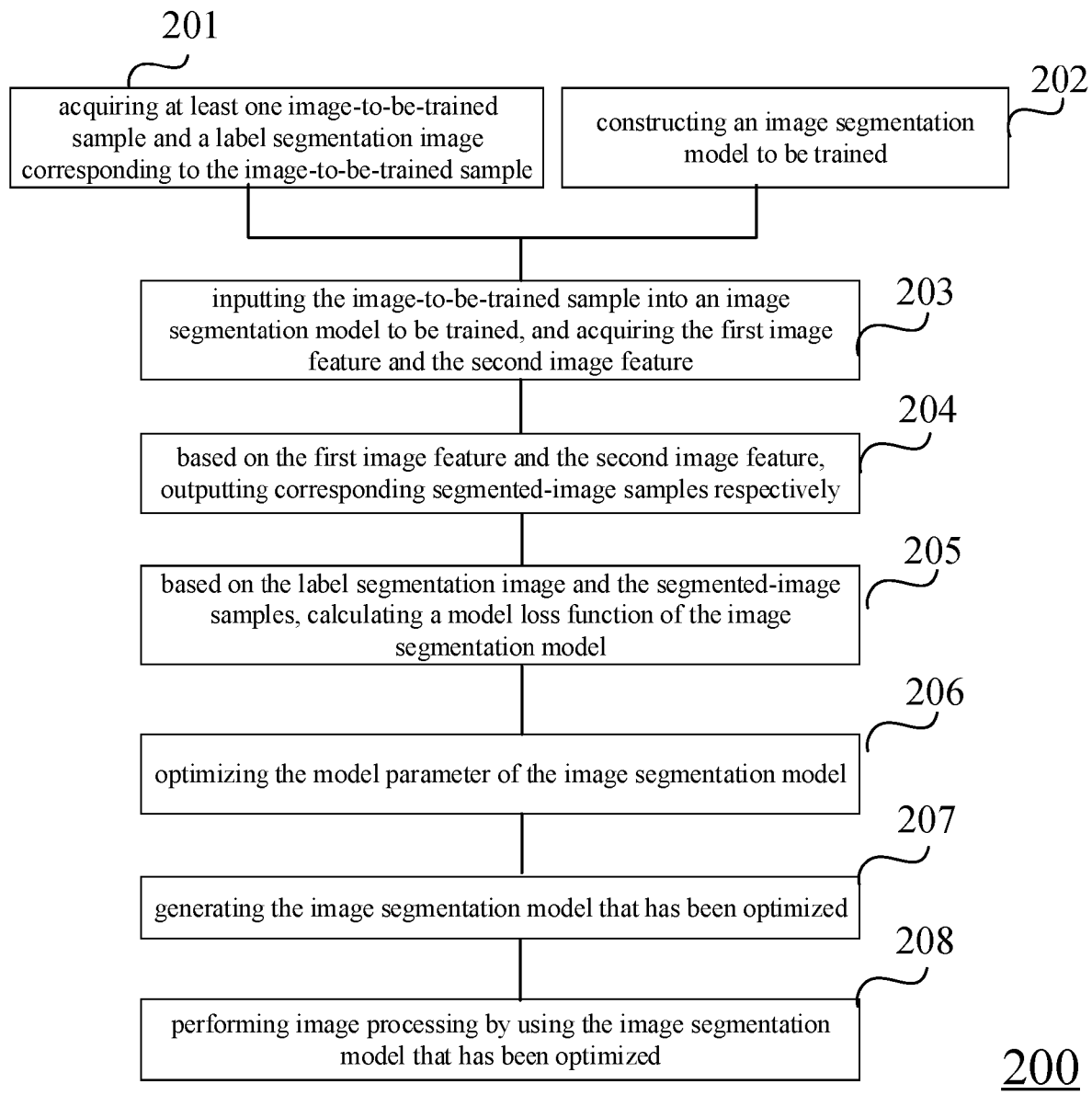
FIG. 2 shows a schematic diagram of the particular flow of the image processing method according to an embodiment 200 of the present application.

As shown in FIG. 2, FIG. 2 is a schematic diagram of the particular flow of the image processing method according to an embodiment 200 of the present application. Taking the technical field of medical image analysis methods as an example, the particular and detailed flow is as follows:

S201: acquiring at least one image-to-be-trained sample and a label segmentation image corresponding to the image-to-be-trained sample.

Here, the image-to-be-trained sample according to the embodiments of the present application takes the brain CT image data of a plurality of patients collected from a hospital or a relevant unit as an example, wherein the datum of the i-th patient is recorded as the image-to-be-trained sample $x_i$, wherein $x_i$ is a three-dimensional matrix C×H×W, wherein H and W are the height and the width of the image-to-be-trained sample $x_i$ respectively, and C is the channel quantity of the image-to-be-trained sample $x_i$. Each image-to-be-trained sample $x_i$ corresponds to one label segmentation image $y_i$ as a real value, wherein $y_i$ is a three-dimensional matrix K×H×W, wherein the value of each of the elements is 0 or 1, is marked by a professional doctor, and is used to mark what disease the patient has, wherein K is the quantity of the disease types within the considered scope, 0 represents no disease, and 1 represents having a disease; in other words, the position marked as 1 of the K-th channel represents that the patient has the K-th type of disease at the position, and the position marked as 0 represents that the patient has no disease.

S202: constructing an image segmentation model to be trained.

In this step, a backbone neural network is constructed as the image segmentation model. The overall structure of the image segmentation model is designed according to a rule of the UNet segmentation network, wherein the model parameter is set to be Θ.

S203: inputting the image-to-be-trained sample into an image segmentation model to be trained, and acquiring the first image feature and the second image feature.

Here, the image-to-be-trained sample is inputted into an image segmentation model to be trained, and, from the output sequence corresponding to the image-to-be-trained sample extracted by using the image segmentation model, the first image feature of the last sequence position and the second image feature of the second last sequence position are selected. Particularly, the image-to-be-trained sample $x_i$ of the i-th patient acquired in the above step is used as the input of the image segmentation model, and sequentially passes through an encoder and a decoder in the image segmentation model. The last one output layer of the decoder outputs the first image feature, and the second last output layer outputs the second image feature. The first image feature and the second image feature are set to be $\{Z_j, j=M-1, M\}$, wherein $Z_{M-1}$ and $Z_M$ are the first image feature and the second image feature respectively. The dimensions of $Z_j$ are $c \times h \times w$ wherein c is the channel dimension, the channel dimensions of the features are generally not 1, and h and w are the height and the width of the features. Here, the two acquired output features are used to participate in the subsequent image prediction, to increase the accuracy of the model prediction.

S204: based on the first image feature and the second image feature, outputting corresponding segmented-image samples respectively.

Here, this step comprises by using a convolution operation in which a convolution kernel is a first numerical value, adjusting individually a channel dimension of the first image feature and a channel dimension of the second image feature to a preset channel-dimension numerical value. Particularly, based on the neural network in the segmentation network model, linear superposition is performed to the characteristic channel dimension by using a convolution operation in which the convolution kernel is a first numerical value such as 1*1, and additionally the channel dimension of $Z_j$ is adjusted to K, so that the image scale of $Z_j$ is K×h×w.

Optionally, this step comprises performing a max-pooling operation to the label segmentation image, and adjusting an image scale comprising the channel dimension of the label segmentation image to a preset image scale comprising the preset channel-dimension numerical value. Particularly, normalization, activation of the maximum value and inhibition of the other small values are performed by using a soft-max activation function along the channel dimension pixel by pixel, wherein $\{p_j\}$ represents a set of the segmented-image samples predicted by $Z_j$. For the subsequent calculation of the model loss function, the image scales of the label segmentation images $y_i$ are individually adjusted to a preset image scale by using a max-pooling operation (MaxPool). The preset channel-dimension numerical value according to the embodiment of the present application is the image scale corresponding to $Z_j$, i.e., the preset channel-dimension numerical value K in the preset image scale K×h×w. Here, the label segmentation image representing the real label is reduced to the size $Z_j$, which may serve as a low-level prior, which can better guide the model training, increase the convergence speed of the model, and increase the accuracy of the model.

S205: based on the label segmentation image and the segmented-image samples, calculating a model loss function of the image segmentation model.

This step comprises calculating a cross-entropy loss between at least one of the label segmentation images obtained after the max-pooling operation and the corresponding segmented-image samples, and using an average value of a sum of a predetermined quantity of the acquired cross-entropy losses as the model loss function of the image segmentation model. Particularly, B image-to-be-trained samples $x_i$ are picked up randomly from the acquired image-to-be-trained samples, and are marked as $x_1, x_2, \ldots, x_B$, and the corresponding label segmentation images $y_i$ are $y_1, y_2, \ldots, y_B$. B data are inputted into the segmented-image model to be trained, and B corresponding segmented-image samples $\{p_j\}_i$ are obtained. By using a Focal Loss loss function (denoted by l), it is obtained that the cross-entropy losses between one label segmentation image and the corresponding segmented-image samples generated individually by the first image feature and the second image feature are:

$$L_1[\{p_j\}i, \tilde{y}_i] = \Sigma_j l[P_j, \text{MaxPool}(\tilde{y}_i)] \qquad \text{formula 1}$$

Further, based on the average value of the sum of a predetermined quantity of the acquired cross-entropy losses, it is obtained that the model loss function of the image segmentation model is:

$$L = \frac{1}{B}\sum_{i=1}^{B} L[\{p_j\}_i, \tilde{y}_i] = \frac{1}{B}\sum_{i=1}^{B} \sum_j l[p_j, \text{MaxPool}(\tilde{y}_i)] \qquad \text{formula 2}$$

S206: optimizing the model parameter of the image segmentation model.

This step comprises initializing the model parameter and a training iteration number of the image segmentation model; performing reverse derivation to the model loss function, updating the model parameter based on a gradient corresponding to the model loss function after the reverse derivation, and accumulating a time quantity of the updating till the training iteration number; and further, executing repeatedly the step of acquiring the at least one image-to-be-trained sample and the label segmentation image corresponding to the image-to-be-trained sample to the step of updating the model parameter based on the gradient corresponding to the model loss function after the reverse derivation, till the current training iteration number is greater than the total training iteration number, stopping the optimization, and saving the current image segmentation model that has been optimized.

Particularly, the model parameter Θ of the segmented-image model is initialized evenly by using an Xavier initializing method, and, at the same time, the training iteration number is set to be t=0, and the total training iteration number E is set. Further, reverse derivation is performed to the model loss function L, to obtain the partial derivative $$\frac{\partial L}{\partial \Theta}$$

or L to the model parameter Θ, reverse gradient propagation is performed by using an Adam optimization method, and the model parameter is updated. Each time the model parameter has been optimized, the training iteration number is set to be t=t+1, and it is determined whether t satisfies the training terminating condition: if t≤E, then executing repeatedly the step of acquiring the at least one image-to-be-trained sample and the label segmentation image corresponding to the image-to-be-trained sample to the step of updating the model parameter based on the gradient corresponding to the model loss function after the reverse derivation; and if t≥E, then obtaining the image segmentation model determined by using the optimized model parameter Θ.

S207: generating the image segmentation model that has been optimized.

S208: performing image processing by using the image segmentation model that has been optimized.

Here, this step comprises inputting an acquired image to be processed into the image segmentation model that has been optimized, and generating segmented images corresponding to the image to be processed. For example, the CT image $x_i$ of a patient to be tested is inputted into the optimized image segmentation model, to obtain the segmented images $p_M$. Further, round functional operation is performed to it to obtain a 0-1 segmentation image, which is the final binarized segmented image corresponding to the image to be processed.

The image processing method according to the embodiments of the present application, by improving the trained image segmentation model based on the existing Unet model, and introducing the deep-supervision method, further improve the quality of the hidden-layer features, increase the segmentation precision, effectively reduce the segmentation errors without increasing the inference time and the computational complexity, and increase the accuracy of the image segmentation.

Further, the image processing solution according to the embodiments of the present application is mainly suitable for the field of medical-image analysis, and aims at the difficult point of the technique of medical image diagnosis, i.e., the following problem. Medical image diagnosis has high requirements on the segmentation precision and the stability. Therefore, currently the interpretation of medical-image data still relies on the interpretation by experienced image doctors. The diagnostic results of such a diagnostic mode are susceptible to the limitation by the personal experience and capacity of the doctors, and the accuracy rate is difficult to be ensured in the processing of data of a large scale due to fatigue. Furthermore, medical-image data have a complicated structure, which results in a very high misdiagnosis rate of the artificial diagnosis. The embodiments of the present application, based on the excellent performance of the deep-supervision method in classification tasks, introduce a suitable hidden-layer-assisted loss function into the image segmentation model. It, by suitably using an assisting classifier as the feedback of the feature quality at the hidden layer, directly influences the updating of the weight of the hidden layer, improves the quality of the hidden-layer features, and significantly reduces the test error. Based on the existing deep-supervision method, based on the encoding-decoding semantic-segmentation network, a downsampling deep-supervision method is proposed, wherein the real label value obtained after the downsampling is used as the target of the deep supervision, and the decoding rule in scale is followed. The deep-supervision method, as a particular regularization method, does not add any additional calculation in deduction. The downsampling deep-supervision method effectively improves the quality of the hidden-layer features, so that the deep neural network can learn information of multi scales during the training, which can increase the training speed, reduce gradient vanishing, facilitate the learning of the features, significantly improve the segmentation precision and the stability of the lesion segmentation model, and effectively improves the diagnosis effect.

In addition, the image segmentation model according to the embodiments of the present application is an improvement on a standard Unet network, by adding the deep-supervision module. The module may be expanded to other segmentation models, is an effective plug-and-play module, has an extensive applicability, and can significantly improve the segmentation precision and the stability based on basic models.

Figure 3:
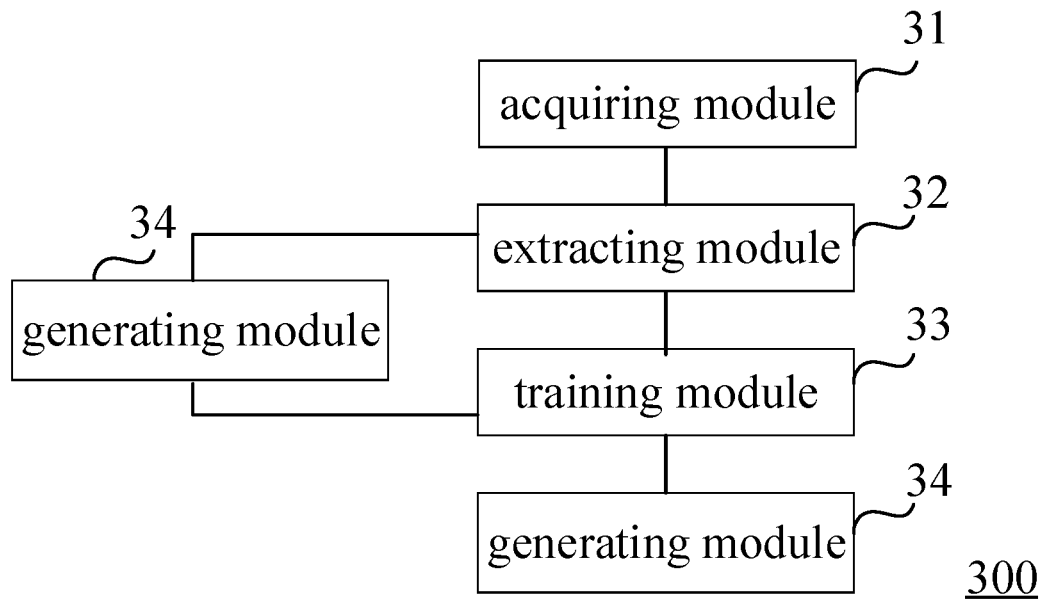
FIG. 3 shows a schematic diagram of the image processing apparatus according to an embodiment 300 of the present application.

On the basis of the same inventive concept, an embodiment 300 of the present application further provides an image processing apparatus, wherein as shown in FIG. 3, the apparatus comprises:

an acquiring module 31 configured for acquiring at least one image-to-be-trained sample and a label segmentation image corresponding to the image-to-be-trained sample;

an extracting module 32 configured for inputting the image-to-be-trained sample into an image segmentation model to be trained, obtaining a first image feature of a last one output layer in the image segmentation model and a second image feature of a second last output layer when the image-to-be-trained sample is being extracted by using the image segmentation model, and based on the first image feature and the second image feature, outputting corresponding segmented-image samples respectively;

a training module 33 configured for, based on the label segmentation image and the segmented-image samples, calculating a model loss function of the image segmentation model, optimizing a model parameter of the image segmentation model by using the model loss function, and generating the image segmentation model that has been optimized; and a generating module 34 configured for inputting an acquired image to be processed into the image segmentation model that has been optimized, and generating segmented images corresponding to the image to be processed.

In the present embodiment, the particular functions and the interaction mode of the acquiring module 31, the extracting module 32, the training module 33 and the generating module 34 may refer to the description on the corresponding embodiments in FIG. 1, and are not discussed here further.

Optionally, the extracting module 32 is further configured for:

by using a convolution operation in which a convolution kernel is a first numerical value, adjusting individually a channel dimension of the first image feature and a channel dimension of the second image feature to a preset channel-dimension numerical value.

Optionally, the apparatus further comprises:

a pooling module 35 configured for performing a max-pooling operation to the label segmentation image, and adjusting an image scale comprising the channel dimension of the label segmentation image to a preset image scale comprising the preset channel-dimension numerical value.

Figure 4:
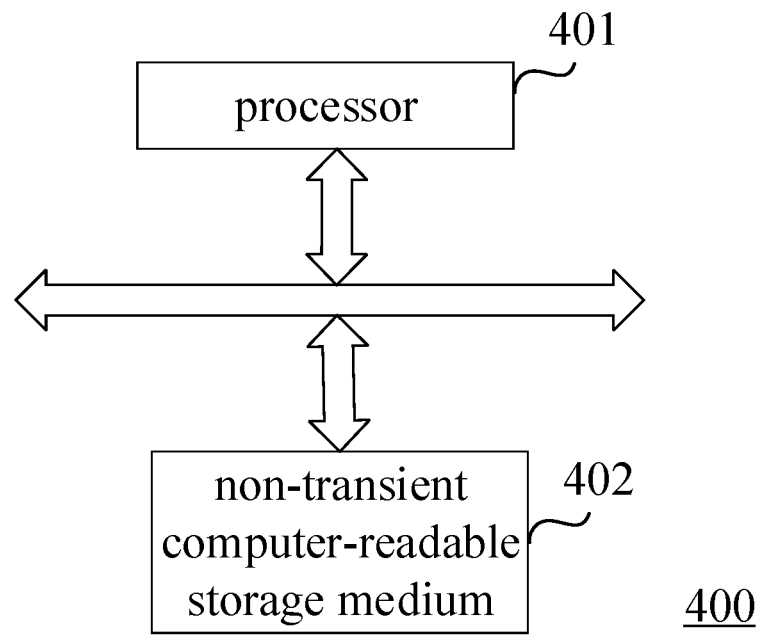
FIG. 4 shows a schematic diagram of the terminal device according to an embodiment 400 of the present application.

As shown in FIG. 4, another embodiment 400 of the present application further provides a terminal device, wherein the terminal device comprises a processor 401, and the processor 401 is configured for implementing the steps of the image processing method stated above. It can be further seen from FIG. 4 that the terminal device according to the above embodiment further comprises a non-transient computer-readable storage medium 402, the non-transient computer-readable storage medium 402 stores a computer program, and the computer program, when executed by the processor 401, implements the steps of the image processing method stated above. In practical applications, the terminal device may be one or more computers, as long as it comprises the above computer-readable medium and processor.

Particularly, the storage medium may be a generic storage medium, such as a mobile disk, a hard disk and a flash memory, and the computer program in the storage medium, when executed, can implement the steps of the image processing method stated above. In practical applications, the computer-readable medium may be comprised in the device, apparatus or system described in the above embodiments, and may also stand alone, and not be installed into the device, apparatus or system. The computer-readable storage medium carries one or more programs, and the one or more programs, when executed, can implement the steps of the image processing method stated above.

According to an embodiment of the present application, the computer-readable storage medium may be a nonvolatile computer-readable storage medium, and, for example, may include but is not limited to: a portable computer disk, a hard disk, a Random Access Memory (RAM), a Read-Only Memory (ROM), an Erasable Programmable Read-only Memory (EPROM or flash memory), a Portable Compact Disc Read-only Memory (CD-ROM), a light storage device, and a magnetic storage device, or any suitable combination of the above, which are not intended to limit the protection scope of the present application. In an embodiment of the present application, the computer-readable storage medium may be any tangible medium containing or storing a program, and the program may be used by or used with an instruction executing system, apparatus or device.

The flow charts and the block diagrams of the drawings of the present application show the system architectures, functions and operations that can be realized by the system, the method and the computer program product according to the embodiments of the present application. In this regard, each of the blocks in the flow charts or the block diagrams may represent part of a module, a program segment or a code, and the part of the module, the program segment or the code contains one or more executable instructions for performing specified logic functions. Further, it should be noted that, in some alternative implementations, the functions marked in the blocks may also be performed in a sequence that is different from that marked in the drawings. For example, two blocks illustrated in succession may actually be executed substantially concurrently, and they sometimes may also be executed in an opposite sequence, which depends on the involved functions. Furthermore, it should be noted that each of the blocks in the block diagrams or the flow charts, and a combination of the blocks in the block diagrams or the flow charts, may be implemented by using a dedicated hardware-based system for performing specified functions or operations, or may be implemented by using a combination of a dedicated hardware and a computer instruction.

A person skilled in the art can understand that the features set forth in the embodiments and/or the claims of the present disclosure may be combined in multiple ways, even if such combinations are not explicitly set forth in the present application. Particularly, the features set forth in the embodiments and/or the claims of the present application may be combined in multiple ways without departing from the spirit and the teaching of the present application, and all of the combinations fall within the scope of the disclosure of the present application.

Finally, it should be noted that the embodiments described above are merely particular embodiments of the present application, and are intended to explain the technical solutions of the present application, and not to limit them, and the protection scope of the present application is not limited thereto. Although the present application is explained in detail with reference to the above embodiments, a person skilled in the art should understand that a person skilled in the art can, within the technical scope disclosed by the present application, easily envisage modifications or variations on the technical solutions set forth in the above embodiments, or make equivalent substitutions to some of the technical features thereof, and those modifications, variations or substitutions do not make the essence of the corresponding technical solutions depart from the spirit and scope of the technical solutions of the embodiments of the present application, and should all be encompassed by the protection scope of the present application. Therefore, the protection scope of the present application should be subject to the protection scope of the appended claims.

What is claimed is:

1. An image processing method, comprising the following steps:
   acquiring at least one image-to-be-trained sample and a label segmentation image corresponding to the at least one image-to-be-trained sample;
   inputting the at least one image-to-be-trained sample into an image segmentation model to be trained, obtaining a first image feature of a last one output layer in the image segmentation model to be trained and a second image feature of a second last output layer in the image segmentation model to be trained when the at least one image-to-be-trained sample is being extracted by using the image segmentation model to be trained, and based on the first image feature and the second image feature, outputting corresponding segmented-image samples respectively;
   based on the label segmentation image and the corresponding segmented-image samples, calculating a model loss function of the image segmentation model to be trained, optimizing a model parameter of the image segmentation model to be trained by using the model loss function, and generating an optimized image segmentation model; and
   inputting an acquired image to be processed into the optimized image segmentation model, and generating segmented images corresponding to the acquired image to be processed.

2. The image processing method according to claim 1, wherein the step of obtaining the first image feature of the last one output layer in the image segmentation model to be trained and the second image feature of the second last output layer when the at least one image-to-be-trained sample is being extracted by using the image segmentation model to be trained comprises:
   by using a convolution operation where a convolution kernel is a first numerical value, adjusting a channel dimension of the first image feature and a channel dimension of the second image feature to a preset channel-dimension numerical value, individually.

3. The image processing method according to claim 2, wherein between the step of, based on the first image feature and the second image feature, outputting the corresponding segmented-image samples respectively and the step of, based on the label segmentation image and the corresponding segmented-image samples, calculating the model loss function of the image segmentation model to be trained, the image processing method further comprises:

performing a max-pooling operation to the label segmentation image, and adjusting an image scale comprising a channel dimension of the label segmentation image to a preset image scale comprising the preset channel-dimension numerical value.

4. The image processing method according to claim 3, wherein the step of, based on the label segmentation image and the corresponding segmented-image samples, calculating the model loss function of the image segmentation model to be trained comprises:

calculating a cross-entropy loss between at least one label segmentation image obtained after the max-pooling operation and the corresponding segmented-image samples, and using an average value of a sum of a predetermined quantity of acquired cross-entropy losses as the model loss function of the image segmentation model to be trained.

5. The image processing method according to claim 4, wherein the step of optimizing the model parameter of the image segmentation model to be trained by using the model loss function comprises:

initializing the model parameter and a training iteration number of the image segmentation model to be trained;
performing a reverse derivation to the model loss function, updating the model parameter based on a gradient corresponding to the model loss function after the reverse derivation, and accumulating a time quantity of updating till the training iteration number; and
executing repeatedly the step of acquiring the at least one image-to-be-trained sample and the label segmentation image corresponding to the at least one image-to-be-trained sample to the step of updating the model parameter based on the gradient corresponding to the model loss function after the reverse derivation, till a current training iteration number is greater than a total training iteration number, stopping an optimization, and saving a current optimized image segmentation model.

6. An image processing apparatus, wherein the apparatus is configured for performing an operations comprising:

acquiring at least one image-to-be-trained sample and a label segmentation image corresponding to the at least one image-to-be-trained sample;
inputting the at least one image-to-be-trained sample into an image segmentation model to be trained, obtaining a first image feature of a last one output layer in the image segmentation model to be trained and a second image feature of a second last output layer in the image segmentation model to be trained when the at least one image-to-be-trained sample is being extracted by using the image segmentation model to be trained, and based on the first image feature and the second image feature, outputting corresponding segmented-image samples respectively;
based on the label segmentation image and the corresponding segmented-image samples, calculating a model loss function of the image segmentation model to be trained, optimizing a model parameter of the image segmentation model to be trained by using the model loss function, and generating an optimized image segmentation model; and
inputting an acquired image to be processed into the optimized image segmentation model, and generating segmented images corresponding to the acquired image to be processed.

7. The image processing apparatus according to claim 6, wherein the operations further comprise:

by using a convolution operation where a convolution kernel is a first numerical value, adjusting individually a channel dimension of the first image feature and a channel dimension of the second image feature to a preset channel-dimension numerical value.

8. The image processing apparatus according to claim 7, wherein the operations further comprise:

performing a max-pooling operation to the label segmentation image, and adjusting an image scale comprising a channel dimension of the label segmentation image to a preset image scale comprising the preset channel-dimension numerical value.

9. A non-transitory computer-readable storage medium, wherein the non-transitory computer-readable storage medium stores an instruction, and the instruction, when executed by a processor, enables the processor to implement the steps of the image processing method according to claim 1.

10. A terminal device, wherein the terminal device comprises a processor, and the processor is configured for implementing the steps of the image processing method according to claim 1.

11. The non-transitory computer-readable storage medium according to claim 9, wherein the image processing method, wherein the step of obtaining the first image feature of the last one output layer in the image segmentation model to be trained and the second image feature of the second last output layer when the at least one image-to-be-trained sample is being extracted by using the image segmentation model to be trained comprises:

by using a convolution operation where a convolution kernel is a first numerical value, adjusting a channel dimension of the first image feature and a channel dimension of the second image feature to a preset channel-dimension numerical value, individually.

12. The non-transitory computer-readable storage medium according to claim 11, wherein the image processing method, wherein between the step of, based on the first image feature and the second image feature, outputting the corresponding segmented-image samples respectively and the step of, based on the label segmentation image and the corresponding segmented-image samples, calculating the model loss function of the image segmentation model to be trained, the image processing method further comprises:

performing a max-pooling operation to the label segmentation image, and adjusting an image scale comprising a channel dimension of the label segmentation image to a preset image scale comprising the preset channel-dimension numerical value.

13. The non-transitory computer-readable storage medium according to claim 12, wherein the image processing method, wherein the step of, based on the label segmentation image and the corresponding segmented-image samples, calculating the model loss function of the image segmentation model to be trained comprises:

calculating a cross-entropy loss between at least one label segmentation image obtained after the max-pooling operation and the corresponding segmented-image samples, and using an average value of a sum of a predetermined quantity of acquired cross-entropy losses as the model loss function of the image segmentation model to be trained.

14. The non-transitory computer-readable storage medium according to claim 13, wherein the image processing method, wherein the step of optimizing the model parameter of the image segmentation model to be trained by using the model loss function comprises:
initializing the model parameter and a training iteration number of the image segmentation model to be trained;
performing a reverse derivation to the model loss function, updating the model parameter based on a gradient corresponding to the model loss function after the reverse derivation, and accumulating a time quantity of updating till the training iteration number; and
executing repeatedly the step of acquiring the at least one image-to-be-trained sample and the label segmentation image corresponding to the at least one image-to-be-trained sample to the step of updating the model parameter based on the gradient corresponding to the model loss function after the reverse derivation, till a current training iteration number is greater than a total training iteration number, stopping an optimization, and saving a current optimized image segmentation model.

15. The terminal device according to claim 10, wherein the image processing method, wherein the step of obtaining the first image feature of the last one output layer in the image segmentation model to be trained and the second image feature of the second last output layer when the at least one image-to-be-trained sample is being extracted by using the image segmentation model to be trained comprises:
by using a convolution operation where a convolution kernel is a first numerical value, adjusting a channel dimension of the first image feature and a channel dimension of the second image feature to a preset channel-dimension numerical value, individually.

16. The terminal device according to claim 15, wherein the image processing method, wherein between the step of, based on the first image feature and the second image feature, outputting the corresponding segmented-image samples respectively and the step of, based on the label segmentation image and the corresponding segmented-image samples, calculating the model loss function of the image segmentation model to be trained, the image processing method further comprises:
performing a max-pooling operation to the label segmentation image, and adjusting an image scale comprising a channel dimension of the label segmentation image to a preset image scale comprising the preset channel-dimension numerical value.

17. The terminal device according to claim 16, wherein the image processing method, wherein the step of, based on the label segmentation image and the corresponding segmented-image samples, calculating the model loss function of the image segmentation model to be trained comprises:
calculating a cross-entropy loss between at least one label segmentation image obtained after the max-pooling operation and the corresponding segmented-image samples, and using an average value of a sum of a predetermined quantity of acquired cross-entropy losses as the model loss function of the image segmentation model to be trained.

18. The terminal device according to claim 17, wherein the image processing method, wherein the step of optimizing the model parameter of the image segmentation model to be trained by using the model loss function comprises:
initializing the model parameter and a training iteration number of the image segmentation model to be trained;
performing a reverse derivation to the model loss function, updating the model parameter based on a gradient corresponding to the model loss function after the reverse derivation, and accumulating a time quantity of updating till the training iteration number; and
executing repeatedly the step of acquiring the at least one image-to-be-trained sample and the label segmentation image corresponding to the at least one image-to-be-trained sample to the step of updating the model parameter based on the gradient corresponding to the model loss function after the reverse derivation, till a current training iteration number is greater than a total training iteration number, stopping an optimization, and saving a current optimized image segmentation model.

* * * * *